US012797315B2

(12) United States Patent
Uehara et al.

(10) Patent No.: US 12,797,315 B2
(45) Date of Patent: Nov. 17, 2026

(54) HYALURONIC ACID-PRODUCTION PROMOTER

(71) Applicant: NISSIN FOODS HOLDINGS CO., LTD., Osaka (JP)

(72) Inventors: Kazuya Uehara, Osaka (JP); Yosuke Sunada, Osaka (JP)

(73) Assignee: Nissin Foods Holdings Co., Ltd., Osaka (JP)

( * ) Notice: Subject to any disclaimer, the term of this patent is extended or adjusted under 35 U.S.C. 154(b) by 287 days.

(21) Appl. No.: 18/552,870

(22) PCT Filed: Jul. 13, 2022

(86) PCT No.: PCT/JP2022/027489

§ 371 (c)(1),
(2) Date: Sep. 27, 2023

(87) PCT Pub. No.: WO2023/286792

PCT Pub. Date: Jan. 19, 2023

(65) Prior Publication Data

US 2024/0180803 A1 Jun. 6, 2024

(30) Foreign Application Priority Data

Jul. 15, 2021 (JP) ................................ 2021-117168

(51) Int. Cl.
*A61K 8/35* (2006.01)
*A61K 8/36* (2006.01)
*A61Q 19/00* (2006.01)

(52) U.S. Cl.
CPC ................ *A61K 8/35* (2013.01); *A61K 8/361* (2013.01); *A61Q 19/007* (2013.01)

(58) Field of Classification Search
CPC .......... A61K 31/12; A61K 31/20; A61K 8/35; A61K 8/361; A61Q 19/007; A23V 2002/00; A23V 2200/318; A23L 33/105; A23L 33/115; A23L 33/12; A23L 33/10; A61P 17/00
See application file for complete search history.

(56) References Cited

FOREIGN PATENT DOCUMENTS

| | | | | | |
|---|---|---|---|---|---|
| CN | 101220329 | A | | 7/2008 | |
| CN | 102488674 | A | * | 6/2012 | |
| CN | 103039988 | A | | 4/2013 | |
| CN | 109890954 | A | | 6/2019 | |
| JP | 2005-343882 | A | | 12/2005 | |
| JP | 2006-347984 | A | | 12/2006 | |
| JP | 2010-90035 | | | 4/2010 | |
| JP | 2010-195827 | A | | 9/2010 | |
| JP | 2011-195504 | A | | 10/2011 | |
| JP | 2014024819 | A | * | 2/2014 | |
| JP | 2014-233202 | | | 12/2014 | |
| KR | 20120032373 | A | * | 4/2012 | A61K 31/12 |
| WO | 2005/059114 | A1 | | 6/2005 | |
| WO | 2011/115061 | A1 | | 9/2011 | |
| WO | WO-2011108821 | A2 | * | 9/2011 | A61P 17/00 |
| WO | WO-2014084670 | A1 | * | 6/2014 | A61K 9/1274 |

OTHER PUBLICATIONS

WO2011/108821A2 English Translation (Year: 2011).*
CN102488674A English Translation (Year: 2012).*
KR20120032373A_English_Translation (Year: 2012).*
JP2014024819A_English_Translation (Year: 2014).*
"The Chinese Graphical Plant Department", Ed. Shore Bacon, Chen China, Lake Science and Technology Press, Sep. 2020, (p. 464) with English translation, 5 pages.
Yaron et.al., "Hyaluronic Acid produced by Human Synovial Fibroblasts", Arthritis and Rheumatism, vol. 19, No. 6, 1976, pp. 1315-1320.
Office Action issued in Chinese Patent Application No. 202280025192.4 on Sep. 30, 2025 (with English translation), 15 pages.
Li, et al, "Study on the interaction of hyaluronidase with certain flavonoids", Journal of Molecular Structure, vol. 1241, Oct. 5, 2021, 130686, 8 pages with English translation.
Kakegawa, et al., "Inhibitory Effects of Some Natural Products on the Activation of Hyaluronidase and Their Anti-allergic Actions", Chem. Pharm. Bull, vol. 40(6), Jun. 1992, 16 pages with English translation.
Honda, et al., "Enhanced Effect of Hyaluronan and Elastin Synthesis in Fibroblasts Through Lipopolysaccharide-activated Macrophages", Anticancer Research, vol. 40, 2020, 6 pages with English translation.
Buhren, et al., "Dose- and time-dependent effects of hyaluronidase on structural cells and the extracellular matrix of the skin", European Journal of Medical Research, vol. 25: 60, 2020, 14 pages with English translation.
International Search Report received for PCT Application No. PCT/JP2022/027489, mailed on Sep. 27, 2022, 5 pages with English translation.
Laurent et al., "Hyaluronan", The FASEB Journal, vol. 6, Apr. 1992, pp. 2397-2402.
Mamoru Kimura, "Absorption of Orally Administered Hyaluronan", Functional Food Research, vol. 14, 2018, pp. 30-35.

(Continued)

*Primary Examiner* — Sarah Pihonak
*Assistant Examiner* — Padmaja S Rao
(74) *Attorney, Agent, or Firm* — Grüneberg Global IP, PLLC

(57) ABSTRACT

An object is to provide a method of indirectly replenishing a decreased amount of hyaluronic acid through taking a substance for promoting the production of hyaluronic acid, other than a method of replenishing a decreased amount of hyaluronic acid by directly orally taking it. A hyaluronic acid-production promoter containing isoliquiritigenin as an active ingredient. The hyaluronic acid-production promoter further containing arachidic acid as an active ingredient. Accordingly, the present invention can be expected to prevent skin aging due to the decrease in hyaluronic acid, as well as improve symptoms associated with the decrease in hyaluronic acid in other organs where hyaluronic acid is involved.

1 Claim, No Drawings

(56) References Cited

OTHER PUBLICATIONS

Papakonstantinou et al., "Hyaluronic Acid: A Key Molecule in Skin Aging", Dermato-Endocrinology, vol. 4, No. 3, 2012, pp. 253-258.
Suzuki et al., "Inhibition of Hyaluronidases and Chondroitinases by Fatty Acids", Journal of Enzyme Inhibition and Medical Chemistry, vol. 17, No. 3, 2002, pp. 183-186.
Written Opinion received for PCT Application No. PCT/JP2022/027489, mailed on Sep. 27, 2022, 5 pages with English translation.
Office Action received for Chinese Patent Application 202280025192.4 dated Mar. 21, 2026, 12 pages with English translation.
Wahab, et al., "*Glycyrrhiza glabra* (Licorice): A Comprehensive Review on Its Phytochemistry, Biological Activities, Clinical Evidence and Toxicology", MDPI Plants 2021, 10, 2751, 36 pages.
Ramalingam, et al., "Phytochemical and Pharmacological Role of Liquiritigenin and Isoliquiritigenin from Radix Glycyrrhizae in Human Health and Disease Models", Frontiers in Aging Neuroscience, vol. 10, Article 348, Nov. 2018, 15 pages.
Kape, et al., "Isoliquiritigenin, a Strong nod Gene- and Glyceollin Resistance Inducing Flavonoid from Soybean Root Exudate", Applied and Environmental Microbiology, vol. 58, No. 5, May 1992, p. 1705-1710.
Sanders, T.H., "Peanuts", Encyclopedia of Food Sciences and Nutrition (Second Edition), 2003, 9 pages.
Morgenstern, K., Preserving the Harvest (1), Aug. 23, 2024, 83 pages.
Wang et al. "Hyaluronan Synthase 2 Protects Skin Fibroblasts Against Apoptosis Induced by Environmental Stress." The Journal of Biological Chemistry, vol. 289, No. 46, Nov. 14, 2014, pp. 32253-32265.

* cited by examiner

HYALURONIC ACID-PRODUCTION PROMOTER

TECHNICAL FIELD

The present invention relates to a hyaluronic acid-production promoter.

BACKGROUND ART

Nowadays, studies on skin anti-aging have been widely carried out. Aging is an important factor that causes skin aging, and besides, influences of dryness, oxidation, ultraviolet (UV) rays and the like are examples of direct factors relating to skin aging. Specific phenomena of skin aging are known to be a decrease in mucopolysaccharides such as hyaluronic acid, a cross-linking reaction of collagen, an UV-induced cell injury, and the like.

Note that hyaluronic acid is widely present in organs and tissues such as the skin, joints, ligaments, lungs, kidneys and brain. Specifically for the skin, hyaluronic acid is an important factor for keeping moisture due to its high moisture retention (Non Patent Literature 1). It is also known that no less than 50% of the body's total hyaluronic acid is present in the skin (Non Patent Literature 2).

As methods of replenishing decreased hyaluronic acid, there have been proposed oral intake for taking hyaluronic acid directly from the mouth and percutaneous absorption for taking hyaluronic acid through the skin. There has been a report that the hyaluronic acid orally taken becomes lower molecular weight due to enterobacteria, and then it is absorbed through the intestinal tract and resynthesized in the skin (Non Patent Literature 3). On the other hand, in the case of percutaneous absorption, it is known that hyaluronic acid cannot be absorbed through the skin due to its large molecular weight. Nevertheless, it has been confirmed that hyaluronic acid has the effect of preventing the dryness of the skin thanks to its water retention capabilities.

CITATION LIST

Non Patent Literature

Non Patent Literature 1

Papakonstantinou E., Hyaluronic acid: A key molecule in skin aging, Dermatoendocrinol, 4(3), 253-8, 2012

Non Patent Literature 2

T. C. Laurent and J. R. Fraser, "Hyaluronan," FASEB J, Vol. 6, pp. 2397-2402, 1992

Non Patent Literature 3

Mamoru Kimura, Absorption of orally administered hyaluronan, Functional Food Research 14:30-35, 2018

SUMMARY OF INVENTION

Technical Problem

The molecular weight of normal hyaluronic acid is said to be 800 thousand to 1.2 million. However, the molecular weight of the hyaluronic acid used in Non Patent Literature 3 is 300 thousand, which is smaller than normal hyaluronic acid. It is thus unclear whether similar degradation and resynthesis would occur when the molecular weight increases. In addition, the outcome in Non Patent Literature 3 is resulted from using rats, and it is unclear whether similar behavior would also be observed in human. Further, it is unclear what extent the degraded hyaluronic acid would be used for resynthesis. As described above, it remains unclear whether the decreased hyaluronic acid can be replenished even though hyaluronic acid is directly taken orally.

The present invention has been accomplished in view of the above problems. That is, an object of the present invention is to provide a method of indirectly replenishing a decreased amount of hyaluronic acid through taking a substance for promoting the production of hyaluronic acid, other than a method of replenishing a decreased amount of hyaluronic acid by directly orally taking it.

Solution to Problem

The present inventors have investigated whether there is a substance for promoting the production of hyaluronic acid. The present inventors have newly found that taking isoliquiritigenin promotes the production of hyaluronic acid and accomplished the present invention.

To solve the above problems, the present invention is directed to a hyaluronic acid-production promoter containing isoliquiritigenin as an active ingredient. It is also preferable to further contain arachidic acid as an active ingredient.

According to the configuration, promoting the production of hyaluronic acid compensates the decrease in hyaluronic acid.

Advantageous Effects of Invention

According to the present invention, the decreased hyaluronic acid can be replenished by an indirect method. Accordingly, the decreased hyaluronic acid can be replenished by the method which is different from direct intake whose effect has not been completely understood to date. The present invention can be expected to prevent skin aging due to the decrease in hyaluronic acid, as well as improve symptoms associated with the decrease in hyaluronic acid in other organs where hyaluronic acid is involved.

DESCRIPTION OF EMBODIMENTS

The hyaluronic acid-production promoter as referred to in the present invention can be an agent as long as it has an effect of promoting the production of hyaluronic acid, and it is characterized by containing at least isoliquiritigenin as an active ingredient. It may further contain arachidic acid as an active ingredient as needed.

Here, "isoliquiritigenin" as used in the present invention is one of naturally-occurring organic compounds, and it is known to be a constituent of licorice, a crude drug. As for the isoliquiritigenin to be used in the present invention, those extracted and purified from a natural product may be used, or those industrially chemically synthesized may be used.

To date, there has been no document describing the absorption rate of isoliquiritigenin upon taking, and the effective concentration of isoliquiritigenin has not been revealed. However, the absorption rate of sesamin, also known as a flavonoid, has been revealed, so the absorption rate of isoliquiritigenin can be estimated from that of sesamin to some extent. The plasma concentration of sesamin is known to be at most 2 ng/mL when 25 mg of sesamin is orally taken. Assuming that isoliquiritigenin has the same absorption rate as that of sesamin, the amount of isoliquiritigenin to be taken per day is preferably 0.001 to 3.5 g. more preferably 0.01 to 3.0 g, and further more preferably 0.03 to 1.8 g in the present invention.

Isoliquiritigenin may be used in its solid state, or may be used as a liquid by dissolving in a solvent. Examples of the solvent include an aqueous solution of sodium hydroxide, ethanol and DMSO, and preferable are the aqueous solution of sodium hydroxide or ethanol. In the present invention, isoliquiritigenin is preferably used by dissolving in the aqueous solution of sodium hydroxide in view of operability.

"Arachidic acid" as used in the present invention is known to be a saturated fatty acid contained in peanut oil. Arachidic acid is also known to be generated by hydrogenation of arachidonic acid. As for the arachidic acid to be used in the present invention, those extracted and purified from a natural product may be used, or those industrially chemically synthesized may be used.

As is the case with isoliquiritigenin, the effective concentration of arachidic acid has not been revealed. However, the absorption rate of arachidic acid can be roughly estimated by assuming it based on EPA and DHA, which are also fatty acids, as in estimation for isoliquiritigenin. Assuming that the absorption rate of arachidic acid is the average value of those of EPA and DHA, the amount of arachidic acid to be taken per day is preferably 0.001 to 10.0 mg, more preferably 0.005 to 5.0 mg, and much more preferably 0.01 to 3.3 mg in the present invention.

Arachidic acid may be used in its solid state, or may be used as a liquid by dissolving in a solvent. Examples of the solvent include alcohol such as methanol, ethanol or propanol; ether; and chloroform, and preferable is alcohol. In the present invention, arachidic acid is preferably used by dissolving in ethanol in view of operability.

The form of the hyaluronic acid-production promoter according to the present invention can be solid or liquid, and can be optionally selected according to the usage form of the hyaluronic acid-production promoter of the present invention.

Further, the hyaluronic acid-production promoter according to the present invention can be used by containing in a food or drink product. For example, it can be used in dairy products such as fermented milk, lactic acid drink and butter, processed egg products such as mayonnaise, and baked sweet buns such as butter cake. It can also be suitably used in processed food products such as instant noodles and cookies. In addition to the above, it can be in a formulated form (e.g., powders, granules, capsules, tablets, etc.) by adding an appropriate carrier and an additive as needed.

It is also useful that the hyaluronic acid-production promoter according to the present invention is contained in foods for specified health uses, foods with nutrient function claims, foods with functional claims and the like in addition to general food or drink products.

EXAMPLE

The present invention will now be more specifically described; however, the present invention is not limited to these. In Example, the production capacity of hyaluronic acid was evaluated by using cultured cells.

(Preparation of Reagents)

Reagents were first prepared. First, isoliquiritigenin (manufactured by Tokyo Chemical Industry Co., Ltd.) was dissolved in 0.1 N aqueous solution of sodium hydroxide to be at 10 mM. Arachidic acid (manufactured by SIGMA) was then dissolved in ethanol with a concentration of 95% or higher to be at 10 mM.

(Preparation of Cultured Cell)

Next, preparation of cultured cells was performed. In Example, the preparation was performed with normal human dermal fibroblasts (NHDF). First, using Dulbecco's Modified Eagle Medium (DMEM, manufactured by Gibco) to which 10% heat-inactivated FBS (manufactured by Biowest) and penicillin-streptomycin (manufactured by Invitrogen) were added, NHDF was cultured under the conditions of 37° C., 5% $CO_2$. NHDF cells were then seeded to a 24-well plate at $1.0\times10^5$ cells/well. Thereafter, the NHDF cells were cultured for 72 hours under the conditions mentioned above.

(Production Capacity Evaluation Test of Hyaluronic Acid)

After the cell culture, the culture supernatant was replaced with DMEM containing no FBS. Next, isoliquiritigenin and arachidic acid were serial-diluted in PBS (PBS (−) pH 7.4, manufactured by Gibco) and each of compounds was added alone or as a solution obtained by mixing them in equal concentration, to be at final concentrations of 0.001 μM, 0.01 μM, 0.05 μM, 0.1 μM and 1 μM. Note that in cultured cells, the concentration is not related to an absorption rate, which is applied to oral intake. Therefore, the concentrations of the compounds to be added were determined as the concentrations mentioned above based on the preferable range mentioned above.

After the addition of the reagent or reagents, the cells were cultured for 24 hours under the conditions of 37° C., 5% $CO_2$. The medium was recovered after culturing, and the concentration of the hyaluronic acid in the culture supernatant was measured using Hyaluronan DuoSet Kit (manufactured by R&D Systems). Note that the cell culture without reagent was set as a negative control (NC) in Example. The production capacity of hyaluronic acid was evaluated with the NC taken as 100%.

The result is shown in Table 1.

TABLE 1

| | 0.001 μM | 0.01 μM | 0.05 μM | 0.1 μM | 1 μM |
|---|---|---|---|---|---|
| Isoliquiritigenin | 118% | 142% | 138% | 112% | 127% |
| Arachidic acid | 111% | 122% | 102% | 107% | 127% |
| Isoliquiritigenin + Arachidic acid | 127% | 173% | 173% | 129% | 116% |

As can be seen in Table 1, the promotion of hyaluronic acid production was confirmed at any concentration when isoliquiritigenin was added. The concentrations from 0.01 to 0.05 μM resulted in remarkably high promotion capacity of production. Next, the concentrations of 0.01 μM or less and of 1 μM resulted in high promotion capacity of production when arachidic acid was added. That is, the result suggested that the hyaluronic acid production was promoted even in the case of adding isoliquiritigenin or arachidic acid alone.

Next, the effect of combination use of isoliquiritigenin and arachidic acid was verified. With reference to Table 1, the combination use was found to promote the hyaluronic acid production better than in the cases of adding each of the compounds alone, at any concentration of 0.1 μM or less. Specifically at the concentrations from 0.01 μM to 0.1 mM, the hyaluronic acid production was promoted better than in the cases of adding each of the compounds alone.

Subsequent to the above, promotion capacity of hyaluronic acid production using compounds other than isoliquiritigenin was studied. Trans-p-coumaric acid, liquiritigenin, and daidzein were used for the study. These substances have characteristics that the structures are similar to those of substances appearing in the metabolic pathway originated from phenylalanine to the production of daidzein, or that of isoliquiritigenin.

As for the study method, the amount of hyaluronic acid produced in the culture supernatant was measured using the same procedure as in the above test except that each reagent was prepared to final concentration of 1 μM. Here, the cell culture without reagent was set as a negative control (NC), and the amount (ng/mL) of hyaluronic acid produced was determined by subtracting the amount of hyaluronic acid produced of the NC from the amount of hyaluronic acid produced of each compound with reagent. The result is shown in Table 2.

TABLE 2

| | Measured value (ng/mL) | Amount of hyaluronic acid produced obtained by subtracting NC (ng/mL) |
|---|---|---|
| NC | 942 | 0 |
| trans-p-coumaric Acid | 1217 | 275.4202 |
| Isoliquiritigenin(ILG) | 1504 | 562.7006 |
| Liquiritigenin | 1106 | 164.725 |
| Daidzein | 891 | 0 |

The result in Table 2 revealed that the amount of hyaluronic acid produced due to ILG was the highest even in the case of comparing the substances having similar chemical structures. In addition, the result suggested that the amount produced is reduced when the structure is changed from ILG to liquiritigenin in the metabolic pathway originated from phenylalanine to the production of daidzein.

As described above, it has been suggested that the hyaluronic acid-production promoter according to the present invention can indirectly replenish a decreased amount of hyaluronic acid, other than a method of directly orally taking hyaluronic acid. Accordingly, the present invention can be expected to prevent skin aging due to the decrease in hyaluronic acid, as well as improve symptoms associated with the decrease in hyaluronic acid in other organs where hyaluronic acid is involved.

The invention claimed is:

1. A hyaluronic acid-production promoter, comprising isoliquiritigenin and arachidic acid as active ingredients, wherein a concentration of isoliquiritigenin is 0.01 μM to 0.05 μM and a concentration of arachidic acid is 0.01 μM to 0.05 μM.

* * * * *